United States Patent [19]

Parke

[11] Patent Number: 5,244,658
[45] Date of Patent: Sep. 14, 1993

[54] BIOLOGICAL INOCULANT EFFECTIVE AGAINST APHANOMYCES

[75] Inventor: Jennifer L. Parke, Madison, Wis.

[73] Assignee: Wisconsin Alumni Research Foundation, Madison, Wis.

[21] Appl. No.: 989,931

[22] Filed: Dec. 10, 1992

Related U.S. Application Data

[63] Continuation of Ser. No. 861,991, Feb. 18, 1992, abandoned, which is a continuation of Ser. No. 387,919, Jul. 31, 1989, abandoned, which is a continuation-in-part of Ser. No. 227,810, Aug. 3, 1988, abandoned.

[51] Int. Cl.$^5$ .................. C12N 1/20; A61K 35/66
[52] U.S. Cl. ........................ 504/117; 435/252.1; 435/252.3; 435/252.5; 435/253.3; 424/93 C; 424/93 D; 424/93 K; 424/93 N
[58] Field of Search ............ 424/93; 435/252.1, 252.3, 435/252.5

[56] References Cited

U.S. PATENT DOCUMENTS 3,819,829  6/1974  Mann .
4,588,584  5/1986  Lumsden et al. .
4,798,723  1/1989  Dart et al. .

FOREIGN PATENT DOCUMENTS 1172585  8/1984  Canada .
59-062509  4/1987  Japan .

OTHER PUBLICATIONS

Parke, J. L., "Biological Control of *Aphanomyces euteiches* F. sp. pisi by Bacteria Applied to Pea Seeds," *Phytopathology* (1987) 77:1688 (Abst.).

Parke, J. L., et al., "Biological Control of *Aphanomyces* Root Rot of Peas," Poster presentation at the National Pea Improvement Association Meetings, Oct. 25-26, 1987.

Parke, J. L., "Biological and Cultural Control of Aphanomyces Root Rot of Peas," Oral presentation Feb. 16, 1988 and published abstract in Wisconsin Food Processors Association Proceedings, p. 89.

Levi, C., "Scientists Discover Biological Solution to Root Rot," CALS Quarterly, Summer/Fall 1987.

"Wisconsin Soil Bacteria Test Successful Against Root Rot," Agrichemical Age, p. 25A (Oct, 1987).

Cavaileer, T. D. and J. L. Peterson, "Effects of Various Biological Control Agents on Wilt and Growth of Field Grown China Aster," *Biological and Cultural Tests* (1988) 3:80.

Cavaileer, T. D. and J. L. Peterson, "Effects of Biological Control Agents on Wilt Severity in Greenhouse—Grown China Aster," *Biological and Cultural Tests* (1988) 3:79.

Fantino, M. G. and C. Bazzi, "Azione Antagonista di *Pseudomonas cepacia* Verso *Fusarium oxysporum* F. sp. Cepae," *Informator Fitopatologico (Apr. 1982), 32:55-58*.

Kawamoto, S. O. and J. W. Lorbeer, "Protection of Onion Seedlings from *Fusarium oxysporum* F. Sp. *Cepae* by Seed and Soil Infestation with *Pseudomonas cepacia*," *Plant Disease Reporter*, (Mar. 1976) 60:189-191.

Knudsen, G. R. and H. W. Spurr, Jr., "Field Persistence and Efficacy of Five Bacterial Preparations for Control of Peanut Leaf Spot," *Plant Disease*, (May 1987) 71:442-444.

Spurr, Harvey W., Jr. and Myron Sasser, "Distribution of Pseudomonas cepacia, a Broad Spectrum Antagonist to Plant Pathogens in North Carolina," *Phytopathology*, 72:710 (Abstr.).

(List continued on next page.)

Primary Examiner—Michael G. Wityshyn
Assistant Examiner—Choon Koh
Attorney, Agent, or Firm—Quarles & Brady

[57] ABSTRACT

A bacterial inoculant is disclosed for controlling root rot in peas caused by Aphanomyces fungus. The inoculum is obtained from general bacterial strains including strains of *Pseudomonas cepacia*, *Pseudomonas fluorescens*, *Corynebacterium flaccumfaciens*, and two other Bacillus strains of uncertain taxonomy.

19 Claims, 7 Drawing Sheets

OTHER PUBLICATIONS

Baker, K. F. and Cook, R. J., "Role of the Pathogen in Biological Control," in *Biological Control of Plant Pathogens*, pp. 160–161, The American Phytopathological Society (1982).

Lee, W. H. et al., "Studies on the Seed Bacterization of Sugar Beets 1. Comparative Studies on the Rhizoplane Microfloras of Sugar Beets Grown in Different Soils," *Annals of the Phytopathological Society of Japan*, 14(4):409–415 (1985) (Abstr.).

Gagne, S., et al., "Inhibition de Champignons Phytopathogenes par des Bacteries Isolees du Sol et de la Rhizosphere de Ligumineuses," *Canadian Journal of Microbology* 31(9):856–860 (1985) (Abstr.).

Cho, E. K., "Strategies for Biological Control of Soil-Borne Diseases in Economic Crops in Korea," *Korean Journal of Plant Pathology* 3(4):313–317 (1987) (Abstr.).

BIOLOGICAL INOCULANT EFFECTIVE AGAINST APHANOMYCES

CROSS REFERENCE TO RELATED APPLICATIONS

This application is a continuation of Ser. No. 861,991 filed Feb. 18, 1992, abandoned, which was a continuation of Ser. No. 387,919 filed Jul. 31, 1989 abandoned, which was a continuation in part of Ser. No. 227,810 filed Aug. 3, 1988, abandoned.

FIELD OF THE INVENTION

The present invention is generally directed to inoculants for plants, and particularly directed to a biological inoculant effective in controlling root rot of plants, such as peas, caused by the fungus *Aphanomyces euteiches*.

BACKGROUND OF THE INVENTION

Farm crops are continually plagued by a variety of pests which can stunt or damage crop growth or even completely destroy the crop. Some of the pests are in the form of weeds which grow similarly to the desired plant and compete for the nutrients provided by soil and water. Other pests are in the form of pathogens such as fungi and bacteria which are found in association with many plants.

One of the more serious problems associated with fungal pathogens in plants is root rot. For example, pea root rot caused by the fungus *Aphanomyces euteiches* is a serious problem in pea-growing areas, particularly in Wisconsin and other Great Lake states. The Aphanomyces fungus infects not only peas, but also snap beans and alfalfa, accounting for 10 to 15% losses in yield. In extreme cases, some fields, where the fungus population has been built up over the period of several years, have become essentially useless for these crops.

Despite efforts to develop fungicides and commercially acceptable pea cultivars with resistance to this pathogen, there is presently no commercially available product capable of controlling Aphanomyces. Currently, the best way to avoid the disease loss is to avoid planting susceptible crops in soils with a high population of the Aphanomyces fungus. Unfortunately, the fungus can survive for many years in field soil and a long rotational time to other crops is not practical. As a result, there is a need to find an alternative disease control strategy to eliminate root rot caused by Aphanomyces and possibly other fungi.

There is increasing interest in the use of living organisms to control such diseases. Microscopic organisms are present in soil in populations of approximately 1 billion per cubic inch of soil. Some of the microorganisms cause disease and some are beneficial. The beneficial microorganisms are of major interest. It has long been known in agriculture that certain of these microbial inoculants can be used to facilitate the growth of certain plant species or to assist the plants in suppressing particular pathogenic organisms. For example, it has been a common practice to inoculate soybeans and other legumes at planting with bacterial cultures of the genus Rhizobium so that nitrogen-fixing nodules will form as a result of the plant-bacterium symbiosis.

Reference is now made to U.S. Pat. No. 4,588,584 to Lumsden, et al. which discloses a particular species of *Pseudomonas cepacia* which is effective in controlling Pythium diseases of cucumber and peas. There is also much literature on the use of *Pseudomonas fluorescens* as a biocontrol agent against various plant diseases, but not against the fungus Aphanomyces. The term "biocontrol agent", as used herein, refers to a living organism which controls diseases.

SUMMARY OF THE INVENTION

It is therefore an object of the invention to provide a biocontrol agent which is effective in biologically controlling pea root rot in the field.

It is also an object of the present invention to provide a biocontrol agent which is effective in reducing plant mortality in peas and other vegetable and field crops.

It is further an object of the present invention to provide a process for increasing the crop yield in Aphanomyces-infested soils.

These and other objects are met by the present invention which is directed to a process for controlling Aphanomyces fungal diseases of plants by inoculating the plants with an effective amount of an essentially biologically pure culture of a bacterial strain selected from the group consisting of strains AMMA, AMMD, PRA25, 5A, AM, CRK419, and mixtures thereof to control Aphanomyces.

The present invention is also directed to a process for increasing seed germination, decreasing plant mortality and increasing yield of a pea plant by inoculating the pea plant with a growth promotional effective amount of an essentially biologically pure culture of a bacterial strain selected from the group consisting of *Pseudomonas cepacia* and *Pseudomonas fluorescens*.

The present invention is also directed to a biological inoculant for controlling Aphanomyces fungal diseases on plants comprising an essentially biologically pure culture of a bacteria selected from the group consisting of strains AMMA, AMMD, PRAZ5, 5A AM, CRK419, and mixtures thereof.

The present invention is also directed to an agriculturally useful composition comprising a pea seed inoculated with an inoculant of either *Pseudomonas cepacia* or *Pseudomonas fluorescens*.

The inoculum which controls Aphanomyces on field crops, such as peas, is also disclosed in this invention. As used herein, the term "inoculum" means a biological control agent which is introduced onto a host substance or into soil. The inoculum comprises an essentially biologically pure culture of the bacteria mentioned in the previous paragraphs.

The bacterial strains and their process of use, disclosed in the present invention, represent a significant advance in controlling Aphanomyces. Because the bacterial strains are a biologically pure culture of a natural biological organism, massive quantities of the inoculum can be applied to the Aphanomyces infested area with little danger of environmental contamination. In view of public concern for ground water contamination and aerial pollution from pesticides, the form of control disclosed in the present invention is an attractive and economic alternative to chemical pesticides and other methods of control.

Other objects, advantages and features of the present invention will become apparent from the following specification when taken in conjunction with the accompanying drawing.

DETAILED DESCRIPTION OF THE INVENTION

Figure 1:
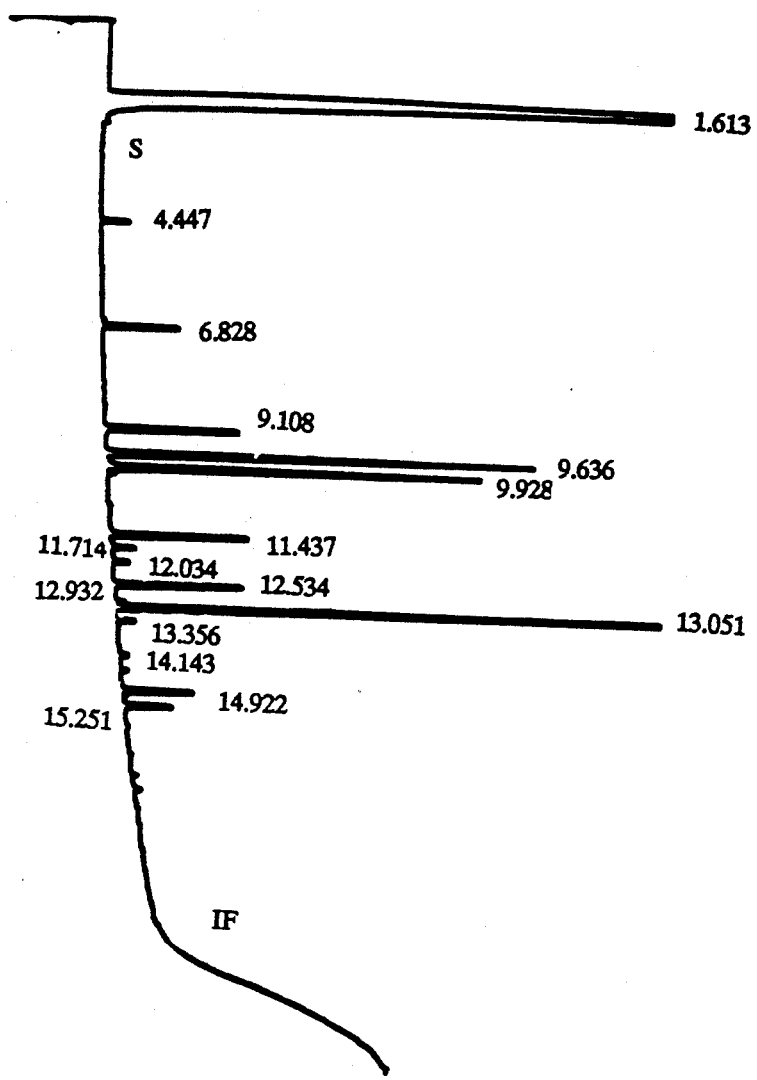
FIG. 1 is a graph illustrating the results of the mass spectrometric analysis of the fatty acid profile of *Pseudomonas cepacia* AMMA.

The present invention is directed to improving the growth and survival rate of field crops infested with the fungus Aphanomyces, and particularly the strain *Aphanomyces euteiches*, by inoculating the field crop with a biologically pure bacterial inoculant of the selected strains of the species *Pseudomonas cepaci, Pseudomonas fluorescens, Corynebacterium flaccumfaciens*, and a strain of *Bacillus*. The particular strains of the bacteria involved in the present invention were discovered by the inventor and are identified by the following nomenclature, as presently known:

Pseudomonas cepacia AMMA
Pseudomonas cepacia AMMD
Pseudomonas fluorescens PRA25
Corynebacterium flaccumfaciens 5A
Bacillus/Corynebacterium sp AM
Bacillus CRK419

The above-referenced bacterial strains were initially isolated from over 200 strains of bacteria associated with pea plants in the field. The bacterial strains *Pseudomonas fluorescens* PRA25 and strains 5A and AM were initially isolated from the rhizosphere of healthy appearing pea plants grown in soil at the University of Wisconsin - Arlington Experimental Farms Pea Root Rot Nursery, a naturally infested pea root rot area. The bacterial strains Pseudomonas cepacia AMMA and *Pseudomonas cepacia* AMMD were initially isolated from the rhizosphere of healthy appearing pea plants grown in containment in soil known to be infested with the *Aphanomyces* fungus from the University of Wisconsin-Arlington Experimental Farm. The strain of uncertain taxonomy (probably Bacillus) designated CRK419 was isolated from a corn field in which peas were previously cultivated near Fredonia, Ozaukee County, Wis.

The targeted bacterial strains were collected in the following manner. The root system from the pea plants was removed and agitated to shake off the excess soil. The hypocotyl and epicotyl segments of the roots were placed in distilled water, sonicated, and thereafter isolated in a plate dilution process, known to the art, in a TSAC (tryptic soy agar cyclohexamide) medium. Cyclohexamide is an anti-fungal agent. Colonies were thereafter selected and screened according to methods known to the art. The bacterial strains were thereafter stored in a DMSO solution at approximately −80° C. until required for use.

It has been found that the bacterial strains may be mass produced in culture with relative ease. The strains are cultured in a suitable culture medium such as a commercially available nutrient broth yeast (NBY) extract. As the bacterial strains grow and multiply, essentially biologically pure cultures of the strains are formed which may be collected. The term "biologically pure culture" is used herein to refer to cultures of bacteria that have essentially no concentration of other strains of bacteria.

The bacteria strains were then screened for biocontrol activity in soil which has been naturally infested or artificially infested with the Aphanomyces fungus in order to determine which bacterial strains are effective biocontrol agents.

The selected biocontrol agents were coated onto the plant seeds, e.g., the pea seeds, prior to planting. A preferred method for coating the seeds is to combine the bacterial strain with a biologically non-interfering liquid carrier for application onto the seeds. A carrier shall be deemed "biologically non-interfering" if it does not prevent the bacterial strains from growing, and if it does not affect Aphanomyces in the absence of the bacteria. The nutrient medium in which the bacteria were cultured has been found to be a satisfactory medium. A suitable fungicide, i.e., captan, may also be coated on the seeds. The cultures survive air-drying after seed coating. The preferred carrier is a water-based liquid, preferably sterile distilled water.

Although coating the seed with the bacterial strain is preferred, other processes which provide a convenient means for distributing the bacterial strain to the Aphanomyces fungi fall within the scope and spirit of the invention. For example, the bacterial strain may be directly applied to the soil prior to planting the seeds.

Whether the inoculant is coated actually on the plant seed or inserted into the furrows into which the seeds are planted, the inoculant is preferably diluted with a suitable carrier or extender so as to make the inoculant easier to handle and to provide a sufficient quantity of material so as to be capable of easy human handling. Examples of suitable carriers include water, granular minerals, such as vermiculite, soils or peat.

To enable others to obtain a culture of these strains, samples have been deposited with the American Type Culture Collection (ATCC), being identified by the accession number and date of deposit as follows:

| Bacterial Strain | ATCC Accession No. | Date of Deposit |
|---|---|---|
| *Pseudomonas cepacia* AMMA | 52796 | 7/22/88 |
| *Pseudomonas cepacia* AMMD | 53795 | 7/22/88 |
| *Pseudomonas fluorescens* PRA25 | 53794 | 7/22/88 |
| *Corynebacterium flaccumfaciens* 5A | 53934 | 7/26/89 |
| Bacillus/Corynebacterium AM | 53933 | 7/26/89 |
| Bacillus CRK419 | 53935 | 7/26/89 |

To further identify the bacterial strains, a fatty acid profile for each rhizosphere culture was determined by mass spectrometric analysis. The term "rhizosphere", as used herein, refers to the zone of soil subject to the influence of the plant roots.

With reference to FIG. 1, the results of the tests to determine the fatty acid profile for *Pseudomonas cepacia* AMMA are presented below in Table 1:

TABLE 1

| RT | Area | Ar/Ht | Respon | ECL | Name | % | Comment 1 | | Comment 2 |
|---|---|---|---|---|---|---|---|---|---|
| 1.613 | 40785000 | 0.081 | — | 7.051 | SOLVENT PEAK | | <min rt | | |
| 4.447 | 1548 | 0.036 | 1.036 | 12.000 | 12:0 | 0.98 | ECL deviates | 0.000 | Ref 0.000 |
| 6.828 | 4415 | 0.038 | 0.969 | 14.000 | 14:0 | 2.63 | ECL deviates | 0.000 | Ref −0.001 |
| 9.108 | 8547 | 0.042 | 0.944 | 15.493 | Sum In Feature 3 | 4.95 | ECL deviates | 0.003 | 14:0 3OH/16:1 ISC |
| 9.636 | 27640 | 0.042 | 0.941 | 15.819 | 16:1 CIS 9 | 15.97 | ECL deviates | 0.002 | |
| 9.928 | 25281 | 0.044 | 0.940 | 15.999 | 16:0 | 14.58 | ECL deviates | −0.001 | Ref −0.002 |
| 11.437 | 9844 | 0.047 | 0.936 | 16.890 | 17:0 CYCLO | 5.66 | ECL deviates | 0.002 | Ref 0.000 |
| 11.714 | 1646 | 0.047 | 0.936 | 17.052 | 16:1 2OH | 0.95 | ECL deviates | 0.005 | |
| 12.034 | 1188 | 0.047 | 0.936 | 17.236 | 16:0 2OH | 0.68 | ECL deviates | 0.001 | |
| 12.534 | 9443 | 0.048 | 0.937 | 17.524 | 16:0 3OH | 5.43 | ECL deviates | 0.004 | |
| 12.937 | 733 | 0.047 | — | 17.757 | | — | | | |
| 13.053 | 73016 | 0.048 | 0.937 | 17.824 | Sum In Feature 7 | 42.01 | ECL deviates | −0.001 | 18:1 TRANS 9/t6/c11 |
| 13.356 | 1307 | 0.046 | 0.938 | 17.998 | 18:0 | 0.75 | ECL deviates | −0.002 | Ref −0.002 |
| 14.143 | 904 | 0.066 | — | 18.452 | — | — | | | |
| 14.922 | 5361 | 0.050 | 0.943 | 18.901 | 19:0 CYCLO C11-12 | 3.10 | ECL deviates | 0.001 | Ref 0.001 |
| 15.251 | 3969 | 0.055 | 0.945 | 19.091 | 18:1 2OH | 2.30 | ECL deviates | 0.003 | |
| ****** | 8547 | — | — | — | SUMMED FEATURE 3 | 4.95 | 12:0 ALDE ? 16:1 ISO I/14:0 3OH | | unknown 10.9 14:0 3OH/ 16:1 ISO I |
| ****** | — | — | — | — | | — | | | |
| ****** | 73016 | — | — | — | SUMMED FEATURE 7 | 42.01 | 18:1 CIS 11/t 9/t 6 | | 18:1 TRANS 9/t6/c11 |
| ****** | — | — | — | — | | — | 18:1 TRANS 6/t9/c11 | | |

| Solvent Ar | Total Area | Named Area | % NAmed | Total Amnt | Nbr Ref | ECL Deviation | Ref ECL Shift |
|---|---|---|---|---|---|---|---|
| 40785000 | 174842 | 173205 | 99.06 | 162924 | 6 | 0.002 | 0.001 |

| TSBA [Rev 2.0] | | |
|---|---|---|
| | Pseudomonas | 0.440 |
| | P. cepacia | 0.440 |
| | P. c. cepacia GC subgroup B | 0.440 |

Comparison with TSBA [Rev 2.0]: Pseudomonas-cepacia-cepacia GC subgroup B Distance: 3.8

```
                  0     5    10    15    20    25    30    35    40  45  50  55   60  65  70  75
12:0              - * - .     .     .     .     .     .     .     .   .   .   .    .   .   .   .
11:0 ISO.3OH.     * -  .     .     .     .     .     .     .     .   .   .   .    .   .   .   .
13:1 AT 12-13     * -  .     .     .     .     .     .     .     .   .   .   .    .   .   .   .
14:0              - +X - - - .     .     .     .     .     .     .   .   .   .    .   .   .   .
16:1 CIS 9        .     .   - - - - - - - - * - - - - - - - - - - .  .   .   .    .   .   .   .
16:1 C            *     .     .     .     .     .     .     .     .   .   .   .    .   .   .   .
16:0              .     .     .     .   - X - - - - * - - - - -   .   .   .   .    .   .   .   .
17:0 CYCLO        .- - - -  X + - - - - .     .     .     .     .   .   .   .    .   .   .   .
17:0              * -   .     .     .     .     .     .     .     .   .   .   .    .   .   .   .
16:1 2OH          - * - .     .     .     .     .     .     .     .   .   .   .    .   .   .   .
16:0 2OH          - * - .     .     .     .     .     .     .     .   .   .   .    .   .   .   .
16:0 3OH          .     - +X - .     .     .     .     .     .     .  .   .   .    .   .   .   .
18:0              - * - .     .     .     .     .     .     .     .   .   .   .    .   .   .   .
19:0 CYCLO        - X + - - - - - - .     .     .     .     .     .  .   .   .    .   .   .   .
C11-12
18:1 2OH          - - * - - .     .     .     .     .     .     .    .   .   .    .   .   .   .
SUMMED            .    - * - .     .     .     .     .     .     .   .   .   .    .   .   .   .
FEATURE 3
SUMMED            .     .     .     .     .     .   .- - - - - * - - - - - - - - X .    .   .   .
FEATURE 7
```

Figure 2:
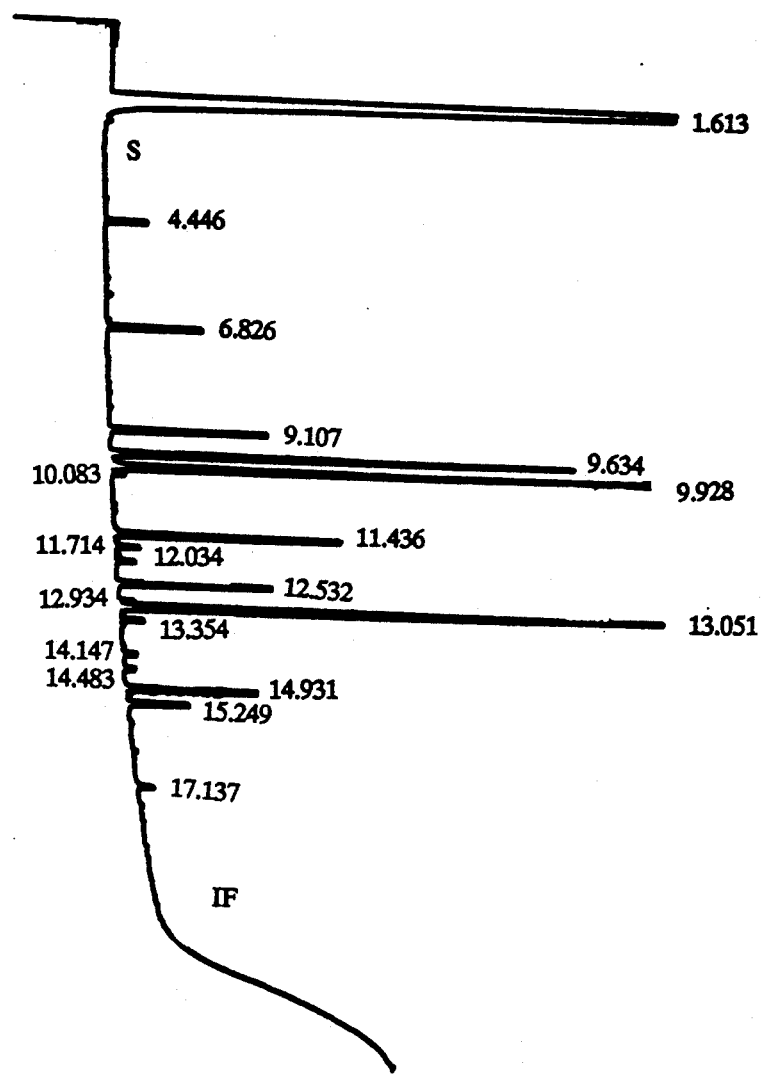
FIG. 2 is a graph illustrating the results of the mass spectrometric analysis of the fatty acid profile of *Pseudomonas cepacia* AMMD.

With reference to FIG. 2, the results of the fatty acid profile for *Pseudomonas cepacia* AMMD are presented below in Table 2:

TABLE 2

| RT | Area | Ar/Ht | Respon | ECL | Name | % | Comment 1 | | Comment |
|---|---|---|---|---|---|---|---|---|---|
| 1.613 | 40748000 | 0.081 | — | 7.052 | SOLVENT PEAK | — | <min rt | | |
| 4.446 | 1993 | 0.031 | 1.036 | 12.000 | 12:0 | 1.00 | ECL deviates | 0.000 | Ref −0.001 |
| 6.826 | 5489 | 0.038 | 0.969 | 14.000 | 14:0 | 2.59 | ECL deviates | −0.000 | Ref −0.002 |
| 9.107 | 9988 | 0.042 | 0.944 | 15.493 | Sum In Feature 3 | 4.59 | ECL deviates | 0.003 | 14:0 3OH/16:1 ISO |
| 9.634 | 30599 | 0.043 | 0.941 | 15.818 | 16:1 CIS 9 | 14.02 | ECL deviates | 0.001 | |
| 9.928 | 36362 | 0.044 | 0.940 | 16.000 | 16:0 | 16.63 | ECL deviates | 0.000 | Ref −0.002 |
| 10.083 | 1560 | 0.070 | — | 16.092 | | — | | | |
| 11.436 | 16563 | 0.048 | 0.936 | 16.890 | 17:0 CYCLO | 7.55 | ECL deviates | 0.002 | Ref 0.000 |
| 11.714 | 1747 | 0.046 | 0.936 | 17.052 | 16:1 2OH | 0.80 | ECL deviates | 0.005 | |
| 12.034 | 1387 | 0.049 | 0.936 | 17.237 | 16:0 2OH | 0.63 | ECL deviates | 0.002 | |

TABLE 2-continued

| RT | Area | Ar/Ht | Respon | ECL | Name | % | Comment 1 | | Comment 2 |
|---|---|---|---|---|---|---|---|---|---|
| 12.532 | 11342 | 0.048 | 0.937 | 17.524 | 16:0 3OH | 5.17 | ECL deviates | 0.004 | |
| 12.934 | 1066 | 0.044 | — | 17.756 | | — | | | |
| 13.051 | 86323 | 0.047 | 0.937 | 17.823 | Sum In Feature 7 | 39.38 | ECL deviates | 0.001 | 18:1 CIS 11/t 9/t6 |
| 13.354 | 1722 | 0.047 | 0.938 | 17.998 | 18:0 | 0.79 | ECL deviates | −0.002 | Ref −0.003 |
| 14.143 | 1445 | 0.067 | — | 18.453 | | — | | | |
| 14.489 | 1051 | 0.057 | — | 18.652 | | — | | | |
| 15.921 | 9636 | 0.048 | 0.943 | 18.901 | 19:0 CYCLO C11-12 | 4.42 | ECL deviates | 0.001 | Ref 0.000 |
| 15.249 | 5288 | 0.057 | 0.945 | 19.091 | 18:1 2OH | 2.43 | ECL deviates | 0.003 | |
| 17.137 | 1003 | 0.043 | — | 20.191 | | — | >max rt | | |
| ****** | 9988 | — | — | — | SUMMED FEATURE 3 | 4.59 | 12:0 ALDE ? 16:1 ISO I/14:0 3OH | | unknown 10.9 14:0 3OH/ 16:1 ISO I |
| ****** | — | — | — | — | | — | | | |
| ****** | 86323 | — | — | — | SUMMED FEATURE 7 | 39.38 | 18:1 CIS 11/t 9/t 6 | | 18:1 TRANS 9/t6/c11 |
| ****** | — | — | — | — | | — | 18:1 TRANS 6/t9/c11 | | |

| Solvent Ar | Total Area | Named Area | % Named | Total Amnt | Nbr Ref | ECL Deviation | Ref ECL Shift |
|---|---|---|---|---|---|---|---|
| 40748000 | 223561 | 218439 | 97.71 | 205479 | 6 | 0.002 | 0.002 |

| TSBA [Rev 2.0] | Pseudomonas | 0.591 |
|---|---|---|
| | P. cepacia | 0.591 |
| | P. c. cepacia GC subgroup B | 0.591 |

Comparison with TSBA [Rev 2.0]: *Pseudomonas-cepacia-cepacia* GC subgroup B-Distance: 3.0

```
                     0    5    10   15   20   25   30   35   40 45 50 55 60 65 70 75
12:0             . *- -  .    .    .    .    .    .    .    .  .  .  .  .  .  .  .
11:0 ISO 3OH.    * -     .    .    .    .    .    .    .    .  .  .  .  .  .  .  .
13:1 AT 12-13    * -     .    .    .    .    .    .    .    .  .  .  .  .  .  .  .
14:0             . +X- - .    .    .    .    .    .    .    .  .  .  .  .  .  .  .
16:1 CIS 9       .       .- - - - - - *- +- - - - - - - -    .  .  .  .  .  .  .  .
16:1 C           *       .    .    .    .    .    .    .    .  .  .  .  .  .  .  .
16.0             .       .    .- - - - - - - X- +- - - -    .  .  .  .  .  .  .  .
17:0 CYCLO       .- - - - - +X- - - -  .    .    .    .    .  .  .  .  .  .  .  .
17:0             * -     .    .    .    .    .    .    .    .  .  .  .  .  .  .  .
16:1 2OH         - * -   .    .    .    .    .    .    .    .  .  .  .  .  .  .  .
16:0 2OH         - * -   .    .    .    .    .    .    .    .  .  .  .  .  .  .  .
16:0 3OH         .   - +X- .    .    .    .    .    .    .  .  .  .  .  .  .  .  .
18:0             - * -   .    .    .    .    .    .    .    .  .  .  .  .  .  .  .
19:0 CYCLO       - - - *- - - - .    .    .    .    .    .  .  .  .  .  .  .  .  .
C11-12
18:1 2OH         - - * - -    .    .    .    .    .    .    .  .  .  .  .  .  .  .
SUMMED           .       - * -    .    .    .    .    .    .  .  .  .  .  .  .  .
FEATURE 3
SUMMED           .       .    .    .    .    .    - - - - +- - - - - X- .  .  .  .
FEATURE 7
```

Figure 3:
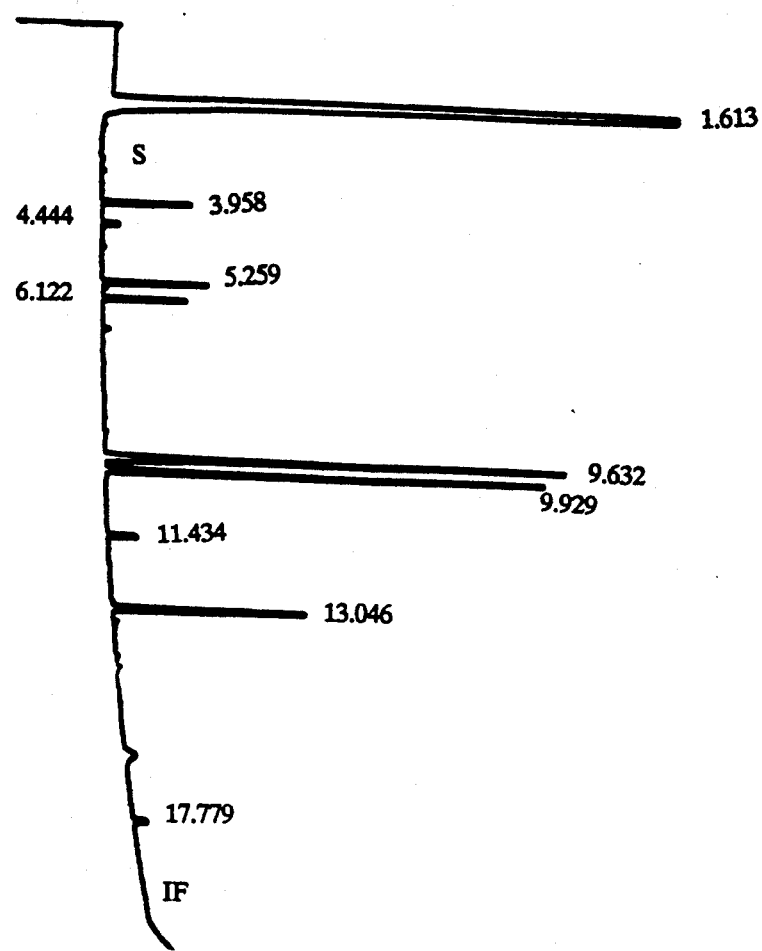
FIG. 3 is a graph illustrating the results of the mass spectrometric analysis of the fatty acid profile of *Pseudomonas fluorescens* PRA25.

With reference to FIG. 3, the results of the tests to determine the fatty acid profile for *Psuedomonas fluorescens* PRA25 are presented below in Table 3:

TABLE 3

| RT | Area | Ar/Ht | Respon | ECL | Name | % | Comment 1 | | Comment 2 |
|---|---|---|---|---|---|---|---|---|---|
| 1.613 | 40050000 | 0.080 | — | 7.047 | SOLVENT PEAK | — | <min rt | | |
| 3.958 | 4169 | 0.030 | 1.069 | 11.429 | 10:0 3OH | 5.14 | ECL deviates | 0.006 | |
| 4.444 | 1045 | 0.039 | 1.041 | 12.000 | 12:0 | 1.26 | ECL deviates | 0.000 | Ref −0.002 |
| 5.759 | 5852 | 0.036 | 0.996 | 13.181 | 12:0 2OH | 6.72 | ECL deviates | 0.003 | |
| 6.122 | 4845 | 0.037 | 0.988 | 13.460 | 12:0 3OH | 5.52 | ECL deviates | 0.005 | |
| 9.632 | 30810 | 0.043 | 0.942 | 16.818 | 16:1 CIS 9 | 33.48 | ECL deviates | 0.001 | |
| 9.925 | 29005 | 0.043 | 0.941 | 15.999 | 16:0 | 31.46 | ECL deviates | −0.001 | Ref −0.002 |
| 11.434 | 1943 | 0.045 | 0.935 | 16.889 | 17:0 CYCLO | 2.10 | ECL deviates | 0.001 | Ref 0.001 |
| 13.046 | 13300 | 0.045 | 0.934 | 17.821 | Sum In Feature 7 | 14.32 | ECL deviates | −0.001 | 18:1 CIS 11/t 9/t6 |
| 17.779 | 528 | 0.026 | — | 20.569 | | — | >max rt | | |
| ****** | 13300 | — | — | — | SUMMED FEATURE 7 | 14.32 | 18:1 CIS 11/t 9/t 6 | | 18:1 TRANS 9/t6/c11 |
| ****** | — | — | — | — | | — | 18:1 TRANS 6/t9/c11 | | |

| Solvent Ar | Total Area | Named Area | % Named | Total Amnt | Nbr Ref | ECL Deviation | Ref ECL Shift |
|---|---|---|---|---|---|---|---|
| 40050000 | 90969 | 90969 | 100.00 | 86707 | 3 | 0.003 | 0.002 |

| TSBA [Rev 2.0] | Pseudomonas | 0.661 (*P. fluorescens* D) |
|---|---|---|
| | P. chlororaphis | 0.661 (*P. fluorescens* D) |
| | P. aureofaciens | 0.515 (*P. fluorescens* E) |

TABLE 3-continued

|   |   |
|---|---|
| P. fluorescens | 0.422 |
| P. f. A. | 0.422 |
| P. f. G. | 0.320 |
| P. f. C. | 0.265 |

Comparison with TSBA [Rev 2.0]: Pseudomonas-chlororaphis (P. fluorescens D)-Distance: 2

|  | 0 | 5 | 10 | 15 | 20 | 25 | 30 | 35 | 40 | 45 | 50 | 55 | 60 | 65 | 70 | 75 |
|---|---|---|---|---|---|---|---|---|---|---|---|---|---|---|---|---|
| 10:0 3OH | . - +X- | | | | | | | | | | | | | | | |
| 12:0 | X +- | | | | | | | | | | | | | | | |
| 12:0 2OH | . - +- X | | | | | | | | | | | | | | | |
| 12:1 3OH | * - | | | | | | | | | | | | | | | |
| 12:0.3OH | . +- X | | | | | | | | | | | | | | | |
| 14:0 | * . | | | | | | | | | | | | | | | |
| 16:1 CIS 9 | | | | | | | | . - X- +- - - - . | | | | | | | | |
| 16:0 | | | | | | | . - - - +X- - - . | | | | | | | | |
| 17:0.CYCLO | - - * - - | | | | | | | | | | | | | | | |
| 18:0 | * - | | | | | | | | | | | | | | | |
| SUMMED FEATURE 7 | | | . - - - X+- - - - . | | | | | | | | | | | | | |

Figure 5:
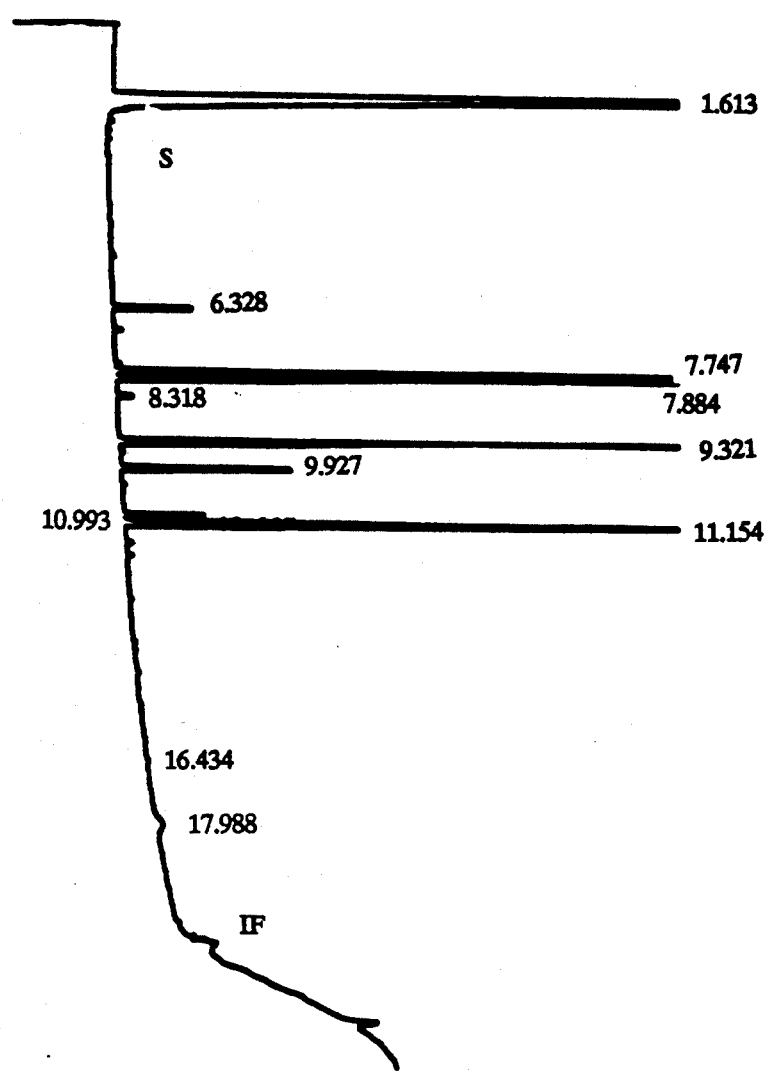
FIG. 5 is a graph illustrating the results of the mass spectrometric analysis of the fatty acid profile of *Corynebacterium flaccumfaciens* 5A.

FIG. 5 illustrates the fatty acid profile, determined by mass spectrometer for strain 5A. The exact taxonomical classification of strain 5A is not certain, although it is in the Corynebacterium or Bacillus groups, and it is currently believed that the organism is properly classified as *Corynebacterium flaccumfaciens*. It is a gram positive, non-motile rod and on NBY forms smooth bright yellow colonies, with margins entire. The bacterial are aerobic, catalese positive, oxidase negative and grow on TTC agar. To further firmly fix the species classification, it would be necessary to perform a thin layer chromatographic analysis of the whole organism methanolysates. The results of the fatty acid analysis are recapitulated in the following Table 4:

TABLE 4

| RT | Area | Ar/Ht | Respon | ECL | Name | % | Comment 1 | | Comment 2 |
|---|---|---|---|---|---|---|---|---|---|
| 1.613 | 40717000 | 0.081 | — | 7.051 | SOLVENT PEAK | | <min rt | | |
| 6.328 | 4354 | 0.036 | 0.979 | 13.618 | 14:0 ISO | 1.23 | ECL deviates | —0.000 | Ref —0.003 |
| 7.747 | 34292 | 0.040 | 0.956 | 14.621 | 15:0 ISO | 9.51 | ECL deviates | —0.000 | Ref —0.002 |
| 7.884 | 198650 | 0.040 | 0.955 | 14.713 | 15:0 ANIEISO | 54.98 | ECL deviates | 0.002 | Ref 0.000 |
| 8.310 | 1069 | 0.043 | 0.950 | 15.000 | 15:0 | 0.29 | ECL deviates | —0.000 | Ref —0.002 |
| 9.321 | 68683 | 0.042 | 0.943 | 15.625 | 16:0 ISO | 18.77 | ECL deviates | —0.001 | Ref —0.003 |
| 9.927 | 11080 | 0.043 | 0.940 | 16.000 | 16:0 | 3.02 | ECL deviates | —0.000 | Ref —0.002 |
| 10.993 | 5560 | 0.045 | 0.937 | 16.629 | 17:0 ISO | 1.51 | ECL deviates | 0.000 | Ref —0.002 |
| 11.150 | 39366 | 0.045 | 0.937 | 16.722 | 17:0 ANIEISO | 10.69 | ECL deviates | 0.000 | Ref —0.003 |
| 16.434 | 1161 | 0.365 | — | 19.784 | — | | >max ar/ht | | |
| 17.908 | 2771 | 0.261 | — | 20.644 | — | | >max rt | | |
| Solvent Ar | Total Area | | Named Area | | % Named | Total Amnt | Nbr Ref | ECL Deviation | Ref ECL Shift |
| 40717000 | 364215 | | 363054 | | 99.68 | 345020 | 8 | 0.001 | 0.002 |
| | TSBA [Rev 2.0] | | | | | Bacillus | | 0.161 | |
| | | | | | | B. polymyxa | | 0.161 | |

Comparison with TSBA [Rev 2.0]: Bacillus-polymyxa   Distance: 5.670

|  | 0 | 5 | 10 | 15 | 20 | 25 | 30 35 40 45 | 50 | 55 | 60 | 65 | 70 | 75 |
|---|---|---|---|---|---|---|---|---|---|---|---|---|---|
| 11:0 ISO3OH. | * - | | | | | | | | | | | | |
| 14:0 ISO | - X +- | | | | | | | | | | | | |
| 14:0 | X - +- | | | | | | | | | | | | |
| 15:0 ISO | | . - - - - - +- - X - | | | | | | | | | | | |
| 15:0 ANIEISO | | | | | | | | | - - - - - - X - - - - +- - - - - - - - - - - - - | | | | |
| 15:0 | * - | | | | | | | | | | | | |
| 16:0 ISO | | . - - - - - - - - +- - - - - - X . | | | | | | | | | | | |
| 16:1 A | X +- - | | | | | | | | | | | | |
| 16:0 | . X - - - +-.- - - | | | | | | | | | | | | |
| 17:0 ISO | . - X +- - | | | | | | | | | | | | |
| 17:0 ANIEISO | | . - - - +- - X | | | | | | | | | | | |

Figure 6:
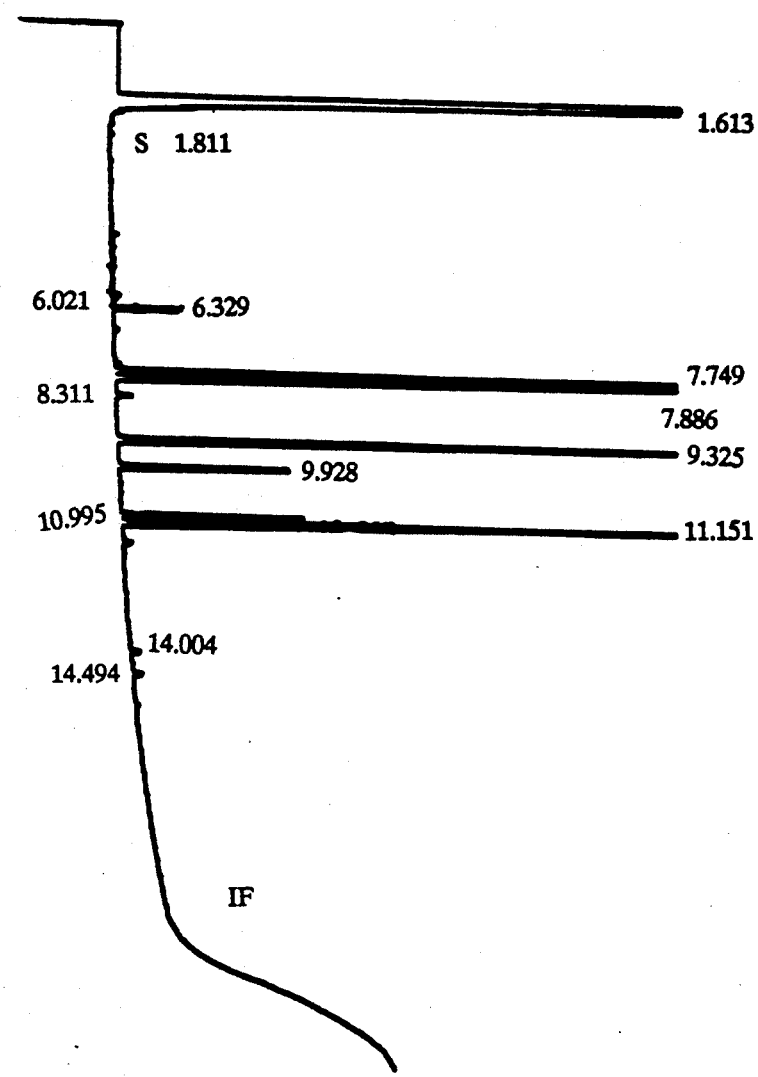
FIG. 6 is a graph illustrating the results of the mass spectrometric analysis of the fatty acid profile of bacterial strain AM.

The strain AM is also not unequivocally classified. It appears to belong to the *Bacillus polymyxa/circulans/macerans* group. It may also, however, be Corynebacterium as well. With reference to FIG. 6, the results of the fatty acid profile for strain AM are presented below in Table 5:

TABLE 5

| RT | Area | Ar/Ht | Respon | ECL | Name | % | Comment 1 | Comment |
|---|---|---|---|---|---|---|---|---|
| 1.613 | 40608000 | 0.081 | — | 7.052 | SOLVENT PEAK | — | <min rt | |
| 1.811 | 815 | 0.020 | — | 7.485 | | — | <min rt | |
| 6.021 | 620 | 0.037 | 0.985 | 13.381 | 14:0 ISO E | 0.15 | ECL deviates −0.007 | Ref −0.002 |
| 6.329 | 3574 | 0.036 | 0.979 | 13.618 | 14:0 ISO | 0.84 | ECL deviates −0.000 | Ref −0.001 |
| 7.749 | 41315 | 0.040 | 0.956 | 14.621 | 15:0 ISO | 9.53 | ECL deviates −0.000 | Ref −0.001 |
| 7.886 | 217290 | 0.041 | 0.955 | 14.713 | 15:0 ANIEISO | 50.05 | ECL deviates 0.002 | Ref 0.001 |
| 8.311 | 968 | 0.042 | 0.950 | 14.999 | 15:0 | 0.22 | ECL deviates −0.001 | Ref −0.001 |
| 9.325 | 82543 | 0.042 | 0.943 | 15.626 | 16:0 ISO | 18.78 | ECL deviates 0.000 | Ref −0.001 |
| 9.928 | 11351 | 0.044 | 0.940 | 15.999 | 16:0 | 2.57 | ECL deviates −0.001 | Ref −0.002 |
| 10.995 | 12426 | 0.044 | 0.937 | 16.629 | 17:0 ISO | 2.81 | ECL deviates 0.000 | Ref −0.001 |
| 11.153 | 66566 | 0.044 | 0.937 | 16.722 | 17:0 ANIEISO | 15.04 | ECL deviates 0.000 | Ref −0.001 |
| 14.004 | 805 | 0.050 | — | 18.372 | | — | | |
| 14.494 | 808 | 0.053 | — | 18.655 | | — | | |

| Solvent Ar | Total Area | Named Area | Total Amnt | % Named | Nbr Ref | Ref ECL Shift |
|---|---|---|---|---|---|---|
| 40608000 | 438266 | 436653 | 414520 | 99.63 | 8 | 0.001 |

TSBA [Rev 2.0]

Comparison with TSBA [Rev 2.0]: *Bacillus-circulans*    Distance: 8.257

| | Bacillus | ECL Deviation |
|---|---|---|
| | *B. circulans* | 0.021 |
| | *B. polymyxa* | 0.021 |
| | | 0.014 |
| | | 0.002 |

Figure 7:
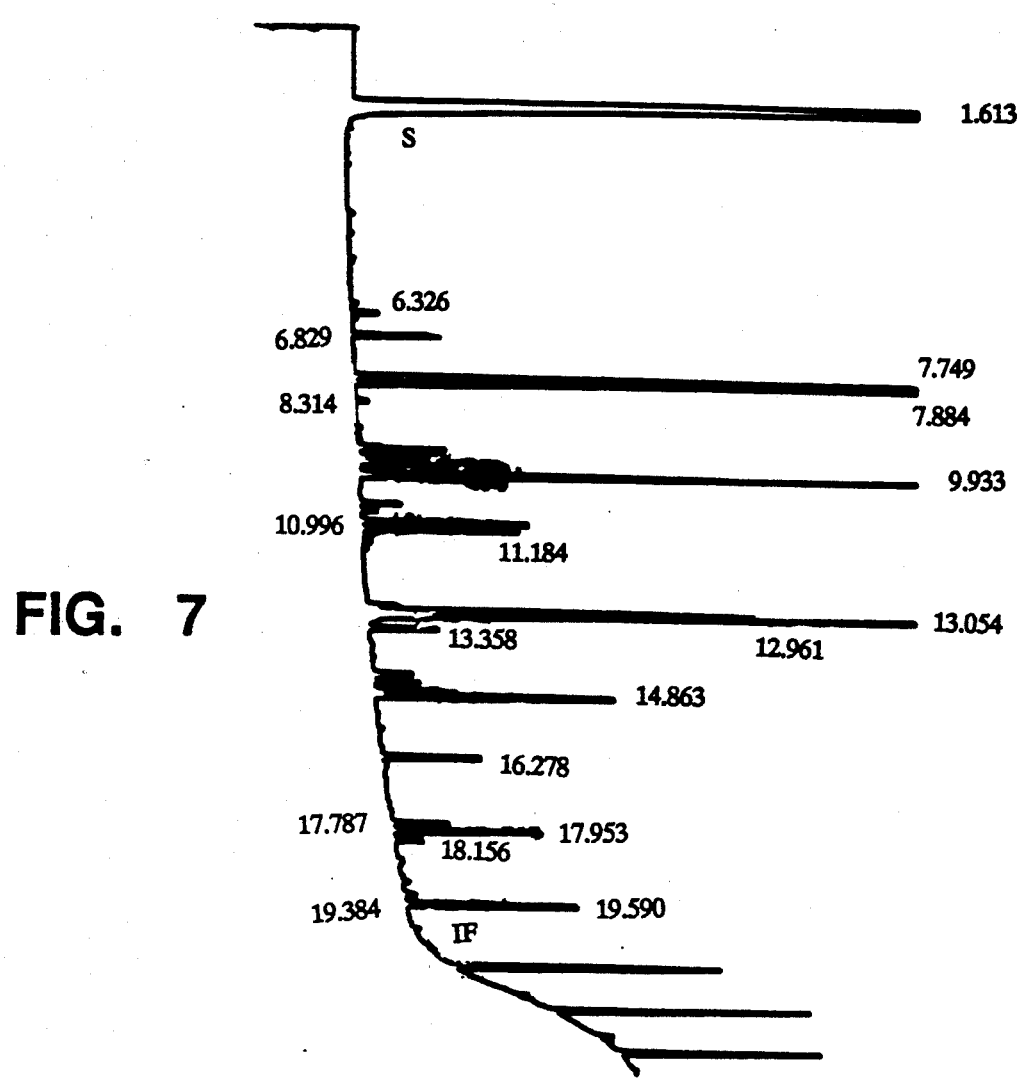
FIG. 7 is a graph illustrating the results of the mass spectrometric analysis of the fatty acid profile of bacterial strain CRK419.

The strain CRK419 is a Bacillus strain, perhaps of *Bacillus firmus*. Referring now to FIG. 7, the results of the fatty acid profile of the Bacillus strain CRK419 is presented referring also to the following Table 6:

TABLE 6

| RT | Area | Ar/Ht | Respon | ECL | Name | % | Comment 1 | Comment |
|---|---|---|---|---|---|---|---|---|
| 1.613 | 40859000 | 0.081 | — | 7.054 | SOLVENT PEAK | | <min rt | |
| 6.326 | 1464 | 0.037 | 0.979 | 13.616 | 14:0 ISO | 0.38 | ECL deviates −0.002 | Ref −0.005 |
| 6.829 | 5020 | 0.038 | 0.969 | 14.002 | 14:0 | 1.28 | ECL deviates 0.002 | Ref 0.000 |
| 7.749 | 33670 | 0.039 | 0.956 | 14.621 | 15:0 ISO | 8.47 | ECL deviates −0.000 | Ref −0.001 |
| 7.884 | 47762 | 0.040 | 0.955 | 14.711 | 15:0 ANIEISO | 12.00 | ECL deviates 0.000 | Ref 0.000 |
| 8.314 | 920 | 0.047 | 0.950 | 15.001 | 15:0 | 0.23 | ECL deviates 0.001 | Ref 0.001 |
| 9.326 | 1334 | 0.037 | 0.943 | 15.626 | 16:0 ISO | 0.33 | ECL deviates −0.000 | Ref 0.000 |
| 9.381 | 6042 | 0.045 | 0.943 | 15.659 | unknown 15.665 | 1.50 | ECL deviates −0.006 | |
| 9.539 | 4827 | 0.046 | 0.942 | 15.757 | 16:1 A | 1.20 | ECL deviates 0.000 | |
| 9.636 | 4396 | 0.044 | 0.941 | 15.817 | 16:1 CIS 9 | 1.09 | ECL deviates 0.000 | |
| 9.695 | 4484 | 0.042 | 0.941 | 156.853 | Sum in feature 4 | 1.11 | ECL deviates −0.003 | 16:1 TRANS 9/15i20H |
| 9.783 | 958 | 0.042 | 0.941 | 15.908 | 16:1 C | 0.24 | ECL deviates −0.000 | |
| 9.933 | 108370 | 0.043 | 0.094 | 16.001 | 16:0 | 26.80 | ECL deviates 0.001 | Ref 0.001 |
| 10.484 | 2818 | 0.046 | 0.938 | 16.385 | 17:1 ISO E | 0.70 | ECL deviates −0.002 | |
| 10.745 | 1397 | 0.054 | 0.937 | 16.480 | Sum in feature 5 | 0.34 | ECL deviates 0.004 | 17:1 ISO I/ANTEI B |
| 10.996 | 11597 | 0.046 | 0.937 | 16.628 | 17:0 ISO | 2.86 | ECL deviates −0.001 | Ref −0.001 |
| 11.154 | 10474 | 0.044 | 0.937 | 16.721 | 17:0 ANIEISO | 2.58 | ECL deviates −0.001 | Ref −0.000 |
| 11.274 | 1078 | 0.058 | 0.936 | 16.792 | 17:1 B | 0.27 | ECL deviates 0.000 | |
| 11.438 | 833 | 0.053 | 0.936 | 16.889 | 17:0 CYCLO | 0.21 | ECL deviates 0.001 | Ref 0.001 |
| 12.866 | 2291 | 0.054 | 0.937 | 17.716 | Sum in feature 6 | 0.56 | ECL deviates −0.004 | 18:2 CIS 9,12/18:0a |
| 12.961 | 26913 | 0.046 | 0.937 | 17.771 | 18:1 CIS 9 | 6.64 | ECL deviates 0.002 | |
| 13.055 | 98867 | 0.048 | 0.937 | 17.825 | Sum in feature 7 | 24.39 | ECL deviates 0.000 | 18:1 TRANS 9/t6/c11 |
| 13.358 | 5115 | 0.049 | 0.938 | 18.000 | 18:0 | 1.26 | ECL deviates 0.000 | Ref −0.001 |
| 14.379 | 3110 | 0.053 | — | 18.591 | — | — | | |
| 14.570 | 3110 | 0.045 | — | 18.701 | — | — | | |
| 14.765 | 4691 | 0.047 | 0.943 | 18.814 | 19:1 TRANS 7 | 1.16 | ECL deviates −0.009 | |
| 14.863 | 17717 | 0.048 | 0.943 | 18.871 | Sum in feature 9 | 4.40 | ECL deviates 0.004 | 19:0 CYCLO C9-10/un |
| 16.278 | 6987 | 0.047 | — | 19.689 | — | — | >max rt | |
| 17.787 | 4189 | 0.049 | — | 20.569 | — | — | >max rt | |
| 17.953 | 10626 | 0.047 | — | 20.665 | — | — | >max rt | |
| 18.156 | 2298 | 0.052 | — | 20.784 | — | — | >max rt | |
| 19.384 | 1248 | 0.069 | — | 21.499 | — | — | >max rt | |
| 19.590 | 12895 | 0.049 | — | 21.619 | — | — | | |
| ****** | 4484 | — | — | — | SUMMED FEATURE 4 | 1.11 | 15:0 ISO 20H/16:1t9 | 16:1 TRANS 9/15i20H |
| ****** | 1397 | — | — | — | SUMMED FEATURE 5 | 0.34 | 17:1 ISO I/ANTEI B | 17:1 ANTEISO B/i |
| ****** | 2291 | — | — | — | SUMMED FEATURE 6 | 0.56 | 18:2 CIS 9,12/18:0a | 18:0 ANTEISO/18:2 |

TABLE 6-continued

| | | | SUMMED FEATURE 7 | 98867 | — | 24.39 | 18:1 CIS 11/t 9/t 6 | 18:1 TRANS 9/t6/c11 | |
|---|---|---|---|---|---|---|---|---|---|
| | | | SUMMED FEATURE 9 | 17717 | — | 4.40 | 18:1 TRANS 6/t9/c11 un 18.846/18.858 | un 18.858/.846/19c | |
| | | | | | | | 19:0 CYCLO C9-10/un | Ref ECL Shift | |
| Solvent Ar | Total Area | Named Area | % Named | Total Amnt | | Nbr Ref | ECL Deviation | 0.002 | |
| 40859000 | 416245 | 403038 | 96.83 | 379910 | | 11 | 0.003 | | |

Comparison with TSBA [Rev 2.0]: *Bacillus firmus*    Distance: 73.724    *NO MATCH*

TSBA [Rev 2.0]

```
                  0     5    10    15    20    25    30    35    40    45    50    55    60    65    70    75
14:0 ISO        X..+.
14:0            .X.++
15:1 ANTEISO A  X+
15:0 ISO           .X
15:0 ANIEISO    X+
15:0            X+
16:1 ISO E      X.+
16:1 ISO.H      *
16:0 ISO        X.
unknown 15.665   +X
16:1 A           X.+
16:1 CIS 9      +X
16:1 C          X+
16:0              .X.+
17:1 ISO.E       X+
17:1 ANIEISO A   *
17:0 ISO          .+X
17:0 ANIEISO    .X+
17:1 B          .*
17:0 CYCLO      .+
18:1 CIS 9      .*   .X
18:0            +X
19:1 TRANS 7    +X
SUMMED FEATURE 4 .*                              .X
SUMMED FEATURE 5 X.
SUMMED FEATURE 6 +X
SUMMED FEATURE 7 +.
SUMMED FEATURE 9 +.   .X
```

The following non-limitative examples are designed to illustrate the present invention:

EXAMPLES

Example 1

Example 1 was conducted to isolate and determine particular bacterial strains which are effective biocontrol agents for the Aphanomyces fungus. Approximately 200 bacterial strains were isolated from pea roots grown in Wisconsin soils infested with Aphanomyces. Each isolate was grown in a nutrient broth (NBY) and coated onto a captan-treated pea seed (Perfection 8221). The term "captan" refers to a fungicide having the chemical name N-(Trichloromethylthio) tetrahydrophthalimide. The coated seeds were air-dried prior to planting.

Figure 4:
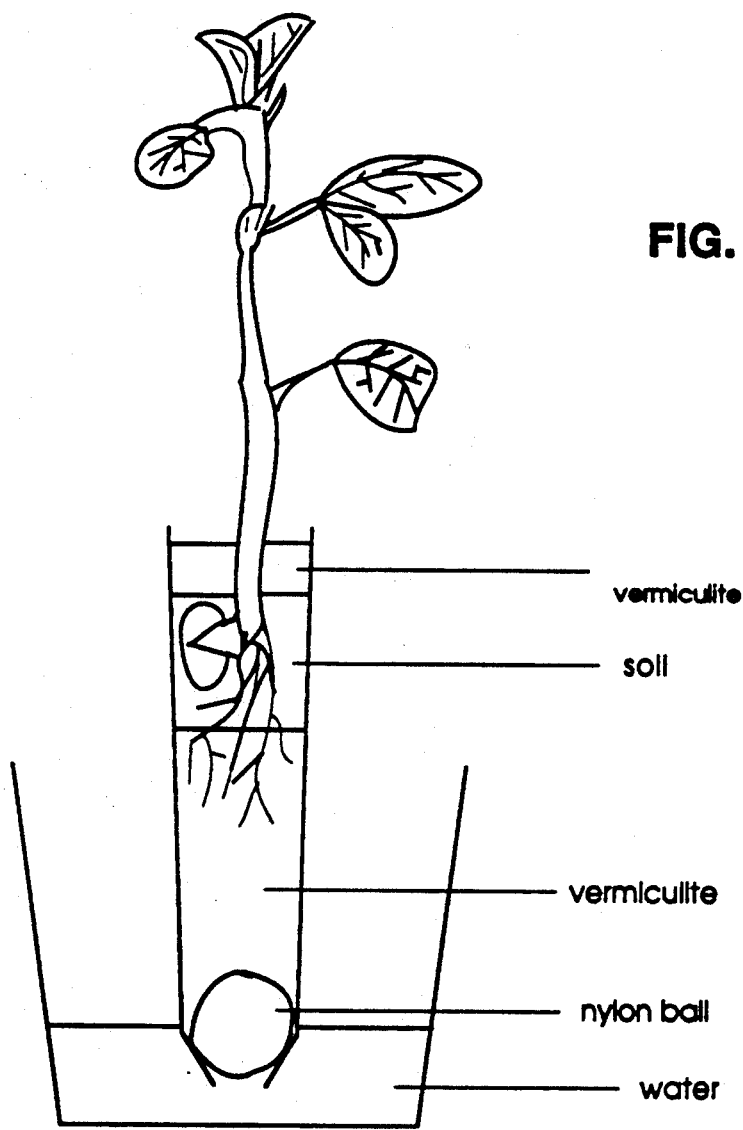
FIG. 4 illustrates a schematic view of a plant bioassay useful for observing biocontrol activity.

The coated seeds and the control seeds were then planted in 60 cc. cone-shaped containers, as illustrated in FIG. 4, containing either pasteurized soil or naturally infested (with Aphanomyces) field soil. Unless otherwise defined, the control in each of the experiments was a captan-treated pea seed. The pasteurized soil was inoculated with $2 \times 10^4$ Aphanomyces zoospores six days after planting. The plants were then grown under greenhouse conditions for approximately three weeks, after which the disease symptoms and shoot dry weights were measured.

The following bacterial strains, listed in Table 7, were identified as the best strains in terms of improvement in shoot dry weights and decreased disease symptoms over control conditions:

TABLE 7

| Bacterial Strain | % Shoot Wt. Increase Compared to Control |
|---|---|
| CRK449 | 19.5 |
| 5A | 19.9 |
| CRK424 | 20.0 |
| AMMD | 20.2 |
| PRA44 | 20.2 |
| CRK419 | 20.6 |
| PRA25 | 21.2 |
| PRA42 | 22.6 |
| PRA48 | 23.0 |
| CRK468 | 25.1 |
| CRK478 | 27.7 |
| PRA15 | 45.2 |
| AMMA | 52.7 |

The bacterial strains which showed the greatest promise in reducing pea root rot and disease severity, as well as increasing shoot dry weight, were then tested under field conditions (Examples 2 and 3).

EXAMPLE 36

Example 2 was designed to test the twelve bacterial strains, which showed the greatest promise from Example 1, for biocontrol activity. The bacterial strains were cultured and coated onto pea seeds according to the methods described in Example 1. The seeds were then planted in a plot of 17 foot rows of 100 seeds each, each replicated 5 times in a randomized block design. The plants were allowed to grow for one season (8 weeks). Plant mortality was evaluated weekly and the plant yield was determined using the dry weight of the pea plants measured. It is to be noted that the disease was so prevalent in this experiment that no pea pods formed. The results of Example 2 are presented below in Table 8.

TABLE 8

| Bacterial Strain | Mean Shoot Dry Wt., g | % Difference** |
|---|---|---|
| control | 61 | — |
| PRA48 | 36 | −41 |
| PRA44 | 44 | −28 |
| CRK424 | 47 | −23 |
| CRK168 | 61 | +1 |
| CRK468 | 66 | +8 |
| PRA42 | 68 | +12 |
| PRA15 | 69 | +22 |
| CRK419 | 79 | +31 |
| PRA25 | 85 | +41 |
| 5A | 92* | +52 |
| AMMD | 94* | +55 |
| AMMA | 103* | +70 |

*P less than .05 Dunnett Test
**Between the treatments (Bacterial Strain) and the control.

EXAMPLE 3

This example, which is similar to Example 2, comprised field trials conducted in locations representing a range of Aphanomyces densities. Example 3 was designed to test five bacterial strains plus a control. The methods and materials were conducted in a manner similar to Example 2. The plant mortality due to Aphanomyces was evaluated weekly. Plant yield was determined using the dry weight of the peas at dry seed stage. The results of this experiment are presented below in Table 9.

TABLE 9

| Bacterial Strain | Mean Dry Wt. Peas, g | % Yield Difference |
|---|---|---|
| control | 175 | — |
| AM | 158 | −10 |
| 5A | 189 | 8 |
| PRA25 | 210 | 12 |
| CRK419 | 215 | 23 |
| AMMD | 282 | 61 |

From Table 3, it can be seen that the bacterial strain AMMD increased the average seed yield by 61%, compared to the non-coated controls.

EXAMPLE 4

Like Example 3, Example 4 was designed to test strains of bacterial in the field. Six bacterial strains plus a control were tested under conditions similar to Example 2. Unlike Example 2, the yield here was determined using the fresh weight of peas. The results of Example 4 can be found below in Table 10:

TABLE 10

| Bacterial Strain | Mean Fresh Wt. Peas, g | % Yield Difference |
|---|---|---|
| control | 105 | — |
| UW85 | 119 | 13 |
| CRK419 | 155 | 41 |
| PRA25 | 166 | 58 |
| 5A | 177 | 69 |
| AMMD | 188 | 79 |
| AM | 209* | 99 |

*P less than .05 Dunnett Test.

Several bacterial strains increased pea yield by 13-99%. *Pseudomonas cepacia* strain AMMD increased yield by 79%, and *Pseudomonas fluorescens* strain PRA 25 increased yield by 58% compared to the control treatment. It is to be noted that none of the bacterial strains increased the pea yield in fields with less than 1 Aphanomyces propagule per gram of soil.

The next experiments, Examples 5-13, were designed to provide information as to how the bacterial strains work. Although the mechanism of biocontrol by the bacteria is unknown, it has been suggested from tests conducted in petri dishes that the biocontrol bacteria produce a substance which limits the growth of the fungus. This substance may act as an antibiotic in reducing the growth of the fungus in the soil.

EXAMPLE 5

Example 5 was conducted to test the effects of the bacterial cultures on the Aphanomyces zoospores. Prior to conducting the test, it was determined that the growth medium, a 1% solution of NBY broth, does not affect the motility of Aphanomyces zoospores. The bacterial strains Pseudomonas cepacia AMMD and Bacillus cereus (UW85) were grown in the NBY growth medium under conditions explained previously with respect to culturing the bacterial strains. The bacterial strains were then diluted to 1% of their original solution and added to a petri dish containing zoospores of the Aphanomyces fungus. The Aphanomyces zoospores were tested for motility after 30 minutes exposure to the bacterial strains, and cyst germination was quantified after 6 hour exposure to the bacterial strains. Cyst germination is a test of the viability of the fungus.

The motility rating scale is as follows:
0 = no motility
1 = a few motile cells
2 = roughly half
3 = most cells motile
4 = full motility as seen at initial release in check treatment.

After 30 minutes exposure to the bacteria and the controls (lake water and 1% NBY broth), the effects on zoospore motility are presented on Table 11:

TABLE 11

| Bacterial Strain | Motility |
|---|---|
| lake water* | 3.0 |
| NBY* | 3.0 |
| Bacillus cereus | 1.6 |
| AMMD | 0.2 |

*Control

Table 12 below illustrates the effect of exposure of the bacterial strains and controls to cyst development in the Aphanomyces fungus after 6 hours:

TABLE 12

| Bacterial Strain | % Germlings |
|---|---|
| NBY* | 58.6 |
| AMMD | 22.6 |
| lake water* | 17.4 |
| Bacillus cereus | 13.6 |

*Control

Replicates of these procedures also demonstrated that AMMA also eliminates zoospore motility in 10 minutes and delays cyst germination.

EXAMPLE 6

Example 6 was conducted to compare the effects of certain bacterial strains with a control treatment in zoospore motility of Aphanomyces fungus. The experimental procedure described in Example 5 was followed. The effects on zoospore motility was observed 10 minutes after the bacterial strains (or control) was added to the Aphanomyces treatment. The results are illustrated below in Table 13.

TABLE 13

| Treatment* | Motility |
|---|---|
| broth alone | 2.0 |
| AM | 2.0 |
| PRA25 | 1.9 |
| CRK419 | 1.9 |
| BC | 1.8 |
| 5A | 1.4 |
| AMMA | 0.0 |
| AMMD | 0.0 |

*Values are means of 5 replicates.

EXAMPLE 7

Example 7 was conducted to compare the effects of different bacterial strains on mycelial growth, zoospore motility and cyst germination of Aphanomyces. The experimental procedure of Example 5 was followed with respect to Example 7. The results of Example 7 are illustrated below in Table 14.

TABLE 14

| Bacterial Strain | Mycelial Growth | Zoospore Motility | Cyst Germination |
|---|---|---|---|
| AMMA | +++* | +++ | +++ |
| AMMD | +++ | +++ | +++ |
| PRA25 | +++ | — | — |
| AM | +++ | — | — |
| CRK419 | —** | — | — |
| 5A | — | + | — |
| UW85 | +*** | — | — |

*cessation of activity
**no change in activity
***slight decrease in activity

EXAMPLE 8

Example 8 was conducted to compare the effects of the bacterial strain Pseudomonas cepacia AMMD with a control (NBY broth) on cyst germination. The procedure of Example 5 was used with respect to Example 8. The results of this experiment are illustrated below in Table 15.

TABLE 15

| Treatment | % Cyst Germination |
|---|---|
| broth alone | 58.6 |
| AMMD | 22.6 |

EXAMPLE 9

Example 9 was designed to test the in vitro effects of Psuedomonas cepacia AMMD on Aphanomyces zoospores. The Pseudomonas cepacia AMMD bacterial strain was compared to three controls: (1) lake water; (2) cell-free filtrate from NBY-AMMD culture: and (3) NBY growth broth alone. All solutions were diluted to 1% of original in milli-Q water. The motility of the zoospores was rated according to the table illustrated in FIG. 5. Table 16 below illustrates the mean of 5 repetitions at 10 and 30 minutes from the following treatments:

Treatment 1—lake water control
Treatment 2—AMMD in NBY broth
Treatment 3—Cell-free filtrate from NBY-AMMD culture
Treatment 4—NBY broth alone

TABLE 16

| Time | Treatment: | 1 | 2 | 3 | 4 |
|---|---|---|---|---|---|
| 10 min. | | | 3.4 | 0 | 3.6 | 2.6 |
| 30 min. | | | 3.8 | 0 | 3.4 | 2.8 |

As illustrated in Table 16, Pseudomonas cepacia AMMD in the NBY broth eliminates zoospore motility after 10 minutes. However, the NBY broth alone and the cell-free cultures of AMMD do not effect zoospore motility.

EXAMPLE 10

Example 10 was conducted to test the effects of sugar beet seeds coated with certain bacterial strains on Aphanomyces cochlioides zoospores. Sugar beet seeds were coated with the bacterial strains and planted in a growth chamber under conditions similar to Example 1. The soils were inoculated 6 weeks later with 20 ml. of 103 zoospores per milliliter of Aphanomyces cochlioides. Approximately 6 weeks later, the plants were harvested and the shoots dried and weighed. The results of the shoot dry weight are illustrated below in Table 17.

TABLE 17

| Treatment | Shoot Dry Wt. (mg)[1] |
|---|---|
| Control | 5330 |
| BC | 4804 |
| 5A | 5716 |
| AMMD | 9199* |
| AM | 11533* |
| AMMA | 11742* |

[1]Values are means of 15 replicates per treatment. Values marked with an asterisk are significantly different than the controls (Dunnett's test p = 0.05).

The bacterial strains Pseudomonas cepacia AMMA, AM, and AMMD significantly increased sugar beet shoot dry weight compared to the control treatment without bacteria.

EXAMPLE 11

Example 11 was conducted to compare the effects of various bacterial strains with or without the addition of captan on the emergence of pea shoots. The tests were conducted in soil naturally infested with Aphanomyces euteiches. Pea seeds were coated with the bacteria using the same procedure as for Example 1. In one experiment, treated seeds were planted into flats of soil in the greenhouse. The next experiment was conducted in the field using only three of the bacteria. In both cases, seeds without bacteria served as the check treatments. The results of Example 11 are shown below in Table 18.

TABLE 18

Effects of Bacteria On Pea Emergence.

| Bacterial Treatment: | None | 5A | PRA25 | AMMA | AM | CRK419 | AMMD |
|---|---|---|---|---|---|---|---|
| Greenhouse Experiment | | | | | | | |
| with captan | 84 e | 79 e | 88 de | 92 e | 85 e | 81 e | 62 c |
| without captan | 13 a | 29 ab | 63 cd | 61 c | 31 b | 25 ab | — |
| Field Experiment | | | | | | | |
| with captan | 88 d | | 92 d | | 88 d | | 89 d |
| without captan | 40 a | | 56 b | | 56 b | | 72 c |

Treatments within each experiment that are not followed by the same letter are significantly different at the P=0.05 level using the Least Significant Difference test.

As illustrated in Table 18, the bacteria strain Pseudomonas cepacia AMMA and Pseudomonas fluorescens PRA25 significantly improved pea emergence from seeds not treated with captan in the greenhouse experiment. Comparing seeds without captan in the field experiment, Pseudomonas cepacia AMMD and Pseudomonas fluorescens PRA25 significantly increased the emergence of peas compared to those without bacteria. None of the bacteria tested improved the emergence of peas treated with captan.

EXAMPLE 12

This example was conducted to examine the effects of strains PRA25 and AMMD on pre-emergence damping off caused by the fungal pathogen Pythium. Four soils naturally invested with Pythium species were used for this greenhouse experiment. Each replicate consisted of 25 pea plants planted in each of four sorts. Pea seeds without captan were coated with PRA25 or AMMD as previously described and planted in flats containing infested soil. Untreated seeds without bacteria or captan, and seeds treated with captan were used as controls. There were three replicates per treatment, and the protocol was repeated three times. Percentage of pea seedling emergence was determined eight days after planting. The results of these experiments are summarized in the following Table 19.

TABLE 19

| | Pea Seedling Emergence in Pythium-infested soils | | | |
|---|---|---|---|---|
| Seed Treatment | Rochelle | Arlington | Hancock | Muck |
| Untreated | 46.7 | 32.0 | 45.7 | 49.7 |
| PRA25 | 72.0 | 51.5 | 81.3 | 42.7 |
| AMMD | 91.5 | 89.8 | 92.9 | 63.5 |
| Captan | 95.5 | 95.1 | 97.3 | 77.8 |

EXAMPLE 13

This example was a test of the effectiveness of these bacterial inoculants derived from pea fields on Pythium ultimum disease in cucumber. Cucumber seeds variety "Straight Edge" were planted into potted soils invested with the pathogenic Pythium and were inoculated with an overnight liquid culture of the strains tested. Cucumber seeds were treated with the commercial standard fungicide "Apron" or with a standard root clonizing bacteria, designated "standard" for controls. In addiiton untreated seeds were planted both in infected and uninfected soils as controls. Emergence and post-emergence damping off are expressed as percentages in the following Tables 20 and 21. Stand represents a percentage of total plants surviving of those planted and vigor was calculated on the mean distance to first leaf compared to the control.

TABLE 20

| Treatment | % Emergence | % Damping-Off | % Stand |
|---|---|---|---|
| Test 1 | | | |
| Uninoculated | 80 | 0 | 80 |
| Inoculated | 68 | 35 | 44 |
| Apron | 96 | 0 | 96 |
| Standard | 90 | 16 | 78 |
| 5A | 90 | 13 | 80 |
| AM | 72 | 21 | 58 |
| AMMA | 92 | 18 | 78 |
| AMMD | 94 | 28 | 70 |
| CRK419 | 64 | 43 | 40 |
| PRA25 | 88 | 16 | 80 |
| Test 2 | | | |
| Uninoculated | 92 | 0 | 92 |
| Inoculated | 70 | 38 | 46 |
| Apron | 98 | 0 | 98 |
| Standard | 98 | 0 | 98 |
| 5A | 89 | 13 | 76 |
| AM | 82 | 2 | 80 |
| AMMA | 96 | 9 | 88 |
| AMMD | 78 | 8 | 72 |
| CRK419 | 72 | 12 | 62 |
| PRA25 | 98 | 0 | 98 |

TABLE 21

| Treatment | % Emergence | % Damping-Off | % Stand | % Vigor |
|---|---|---|---|---|
| Uninoculated | 100 | 0 | 100 | 100 |
| Inoculated | 74 | 15 | 66 | 72 |
| Apron | 100 | 0 | 100 | 104 |
| Standard | 100 | 0 | 100 | 83 |
| AMMA | 98 | 3 | 95 | 92 |
| AMMD | 96 | 0 | 96 | 95 |
| PRA25 | 96 | 2 | 94 | 106 |

It is understood that the invention is not confined to the particular construction and arrangement herein illustrated and described, but embraces such modified forms thereof as come within the scope of the following claims:

What is claimed is:

1. A process for controlling Aphanomyces fungal diseases of plants comprising inoculating the plants with an Aphanomyces disease-controlling effective amount of an essentially biologically pure culture of a bacterial strain selected from the group consisting of *Pseudomonas cepacia* AMMA (ATCC Accession No. 52796), *Pseudomonas cepacia* AMMD (ATCC Accession No. 53795) and mixtures thereof.

2. The process of claim 1 wherein the plants are pea plants.

3. The process of claim 1 wherein the *Pseudomonas cepacia* is diluted in a carrier to no less than effective concentration.

4. A process for controlling Aphanomyces fungal diseases of plants comprising inoculating the plants with an Aphanomyces disease-controlling effective amount of an essentially biologically pure culture of *Pseudomonas fluorescens* PRA25 of the strain Accession No. 53794.

5. The process of claim 4 wherein the plants are pea plants.

6. The process of claim 4 wherein the *Pseudomonas fluorescens* is diluted in a carrier to no less than effective concentration.

7. A process for increasing germination, decreasing mortality and increasing yield of a pea plant comprising inoculating the pea plant with a growth promotional effective amount of an essentially biologically pure culture of a bacterial strain selected from the group consisting of *Pseudomonas cepacia* AMMA (ATCC Accession No. 53796), *Pseudomonas cepacia* AMMD (ATCC Accession No. 53795), *Pseudomonas fluorescens* PRA25 (ATCC Accession No. 53794), and combinations thereof.

8. The process of claim 7 wherein the culture is diluted in a carrier to no less than effective concentration.

9. An agriculturally useful composition comprising a peak seed inoculated with an inoculant of a culture of a *Pseudomonas cepacia* strain selected from the group consisting of AMMA (ATCC Accession No. 53796) and AMMD (ATCC Accession No. 53795).

10. The composition of claim 9 wherein the *Pseudomonas cepacia* inoculant is diluted in a carrier to no less than effective concentration.

11. An agriculturally useful composition comprising a pea seed inoculated with an inoculant of *Pseudomonas fluorescens* PRA25 (ATCC Accession No. 53794).

12. The composition of claim 11 wherein the *Pseudomonas fluorescens* inoculant is diluted in a carrier to no less than effective concentration.

13. A biologically pure culture of *Pseudomonas cepacia* AMMA (ATCC Accession No. 53796).

14. A biologically pure culture of *Pseudomonas cepacia* AMMD (ATCC Accession No. 53795).

15. A biologically pure culture of *Pseudomonas fluorescens* PRA25 (ATCC Accession No. 53794).

16. A biologically pure culture of *Corynebacterium flaccufaciens* 5A (ATCC Accession No. 53934.

17. A biologically pure culture of Bacillus strain AM (ATCC Accession No. 53933).

18. A biologically pure culture of Bacillus strain CRK419 (ATCC Accession No. 53935).

19. A biological inoculant for plants comprising an essentially biologically pure culture of bacteria selected from the group consisting of *Pseudomonas cepacia* AMMA (ATCC Accession No. 53796), *Pseudomonas cepacia* AMMD (ATCC Accession No. 53795), *Pseudomonas Fluorescens* PRA25 (ATCC Accession No. 53794), *Corynebacterium flaccumfacients* 5A (ATCC Accession No. 53934), Bacillus strain AM (ATCC Accession No. 53933), Bacillus strain CRK419 (ATCC Accession No. 53935), and combinations thereof.

* * * * *

UNITED STATES PATENT AND TRADEMARK OFFICE
CERTIFICATE OF CORRECTION

PATENT NO. : 5,244,658
DATED : September 14, 1993
INVENTOR(S) : Jennifer L. Parke It is certified that error appears in the above-identified patent and that said Letters Patent is hereby corrected as shown below:

Column 1, before line 13, the following text should appear:

--STATEMENT REGARDING FEDERALLY SPONSORED RESEARCH

This invention was made with United States Government support awarded by the United States Department of Agriculture (USDA) HATCH Funds. The United States Government has certain rights in this invention. --

Signed and Sealed this

Eighteenth Day of October, 1994

Attest:

BRUCE LEHMAN

*Attesting Officer*    *Commissioner of Patents and Trademarks*